United States Patent
Chen et al.

(10) Patent No.: US 10,253,022 B2
(45) Date of Patent: Apr. 9, 2019

(54) PROCESS FOR THE PREPARATION OF N-[(3-AMINOOXETAN-3-YL)METHYL]-2-(1,1-DIOXO-3,5-DIHYDRO-1,4-BENZOTHIAZEPIN-4-YL)-6-METHYL-QUINAZOLIN-4-AMINE

(71) Applicant: Hoffmann-La Roche Inc., Little Falls, NJ (US)

(72) Inventors: Junli Chen, Shanghai (CN); Yi Ren, Shanghai (CN); Jin She, Shanghai (CN); Lin Wang, Shanghai (CN); Jianhua Yu, Shanghai (CN); Guocai Zhang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/988,570

(22) Filed: May 24, 2018

(65) Prior Publication Data

US 2018/0265505 A1    Sep. 20, 2018

Related U.S. Application Data

(60) Division of application No. 15/216,501, filed on Jul. 21, 2016, now Pat. No. 10,005,770, which is a continuation of application No. PCT/EP2015/051066, filed on Jan. 21, 2015, which is a continuation of application No. PCT/CN2014/071331, filed on Jan. 24, 2014.

(51) Int. Cl.
| | | |
|---|---|---|
| C07D 417/14 | (2006.01) | |
| C07D 305/06 | (2006.01) | |
| C07D 305/08 | (2006.01) | |

(52) U.S. Cl.
CPC ......... *C07D 417/14* (2013.01); *C07D 305/06* (2013.01); *C07D 305/08* (2013.01)

(58) Field of Classification Search
CPC ... C07D 417/14; C07D 305/06; C07D 305/08
USPC ....................................................... 540/522
See application file for complete search history.

(56) References Cited

FOREIGN PATENT DOCUMENTS

| | | |
|---|---|---|
| CN | 105392787 A | 3/2016 |
| JP | 2007-70270 A | 3/2007 |
| JP | 2013-531001 A | 8/2013 |
| JP | 2013-534233 A | 9/2013 |
| JP | 2013-534233 A2 | 9/2013 |
| WO | 2004/074292 A1 | 9/2004 |
| WO | 2012/004270 A1 | 1/2012 |
| WO | 2012/022681 A2 | 2/2012 |
| WO | 2013/020993 A1 | 2/2013 |
| WO | 2013/053658 A1 | 4/2013 |
| WO | 2004/099159 A1 | 11/2014 |
| WO | 2014/184163 A1 | 11/2014 |

OTHER PUBLICATIONS

Trpimir Ivšic et al., A simple enantioselective route toward ®- and (S)-Rolipram via anhydride desymmetrization, Tetrahedron: Asymmetry 24(4):217-222 (Feb. 28, 2013).
International Preliminary Report on Patentability issued in International Application No. PCT/EP2015/051066, dated Jul. 26, 2016, in 9 pages.
International Search Report issued in International Application No. PCT/EP2015/051066, dated Feb. 19, 2015, in 3 pages.
Written Opinion of the International Searching Authority issued in International Application No. PCT/EP2015/051066, dated Feb. 19, 2015, in 8 pages.

*Primary Examiner* — Kahsay Habte
(74) *Attorney, Agent, or Firm* — Lily J. Ackerman

(57) ABSTRACT

The present invention relates to a novel process for the preparation of a compound of the formula (I):

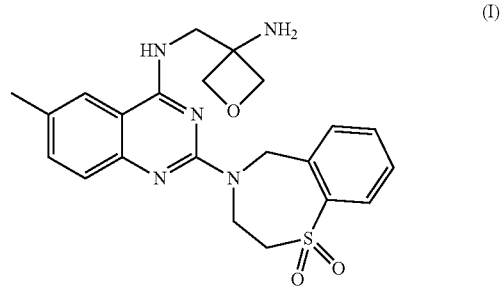

and pharmaceutically acceptable acid addition salts thereof, which is useful for prophylaxis and treatment of respiratory syncytial virus (RSV) infection in mammal or human being.

3 Claims, No Drawings

PROCESS FOR THE PREPARATION OF N-[(3-AMINOOXETAN-3-YL) METHYL]-2-(1,1-DIOXO-3,5-DIHYDRO-1,4-BENZOTHIAZEPIN-4-YL)-6-METHYL-QUINAZOLIN-4-AMINE

CROSS REFERENCE TO RELATED APPLICATIONS

This application is a divisional of U.S. application Ser. No. 15/216,501 filed Jul. 21, 2016, which is a continuation of International Application PCT/EP2015/051066, having an international filing date of Jan. 21, 2015, and which claims benefit under 35 U.S.C § 119 to PCT/CN2014/071331 having an international filing date of Jan. 24, 2014. The entire contents of these applications are hereby incorporated herein by reference.

The present invention relates to a process for the preparation of a compound of the formula (I):

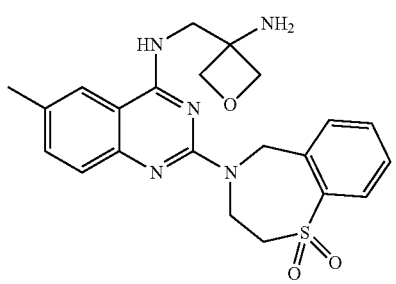

and pharmaceutically acceptable addition salts thereof, which is useful for prophylaxis and treatment of respiratory syncytial virus (RSV) infection in mammal or human being.

Another aspect of the present invention relates to a novel process for the preparation of a compound of the formula (V):

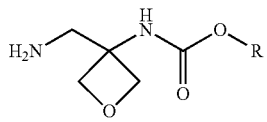

wherein R is $C_{1-6}$alkyl, $C_{1-6}$alkoxyphenyl-$C_xH_{2x}$— or phenyl-$C_xH_{2x}$—. Compound of the formula (V) is important intermediate in the synthesis and manufacture of pharmaceutically active compound of formula (I) as described in patent as described in patent WO2013020993 A1.

BACKGROUND OF THE INVENTION

The patent WO2013020993 A1 disclosed synthetic approaches to obtain compound of formula (I). However, according to the synthetic approach in patent WO2013020993 A1, deprotection of one of the intermediates, 3-(aminomethyl)-N,N-dibenzyl-oxetan-3-amine, for synthesizing compound of formula (I) by hydrogenation with palladium on carbon will lead to heavy metal residual issue, which is not suitable for process chemistry and large scale manufacture. In addition, another intermediate, tert-butyl [(3-aminooxetan-3-yl)methyl] carbamate, for synthesizing compound of formula (I) suffers from instability as the primary amine.

In this invention, a simple and effective synthetic approach is developed to synthesize compounds of formula (I). This synthetic approach can be applied on technical scale and allows to obtain the product in a good yield, desired purity and stable form without using heavy metal catalyst.

DETAILED DESCRIPTION OF THE INVENTION

Definitions

As used herein, the term "$C_{1-6}$alkyl" signifies a saturated, linear- or branched chain alkyl group containing 1 to 6, particularly 1 to 5 carbon atoms, for example as methyl, ethyl, n-propyl, isopropyl, n-butyl, s-butyl, isobutyl, tert-butyl, n-pentyl, 3-methylbutyl, 1,1-dimethylpropyl, n-hexyl, 2-ethylbutyl and the like. Particular "$C_{1-6}$alkyl" groups are tert-butyl and 1,1-dimethylpropyl.

The term "$C_xH_{2x}$" signifies a saturated, linear- or branched chain alkyl group containing 1 to 6, particularly 1 to 4 carbon atoms.

The term "$C_{1-6}$alkoxy" signifies a group $C_{1-6}$alkyl-O—, wherein the "$C_{1-6}$alkyl" is as defined above, for example methoxy, ethoxy, propoxy, iso-propoxy, n-butoxy, iso-butoxy, 2-butoxy, tert-butoxy and the like. Particular "$C_{1-6}$alkoxy" groups are methoxy and ethoxy and more particularly methoxy.

The term "$C_{1-6}$alkoxyphenyl" signifies a phenyl substituted by $C_{1-6}$alkoxy group as defined above at ortho, meta or para position. Particular "$C_{1-6}$alkoxyphenyl" group is 4-methoxyphenyl.

The term "amino" refers to primary (—NH$_2$), secondary (—NH—) or tertiary amino

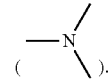

The term "hydroxy" refers to the group —OH.

The term "HA" refers to organic or inorganic acids such as hydrochloric acid, hydrobromic acid, sulfuric acid, phosphoric acid, acetic acid, L-tartaric acid, citric acid, L-lactic acid, maleic acid, fumaric acid, succinic acid, methanesulfonic acid, benzenesulfonic acid, benzoic acid, p-toluenesulfonic acid, oxalic acid, p-nitrobenzoic acid, salicylic acid and 4-chlorobenzoic acid and the like.

The term "acid addition salt" refers to conventional acid addition salts that are formed from suitable non-toxic organic or inorganic acids. Acid addition salts include for example those derived from organic or inorganic acids such as hydrochloric acid, hydrobromic acid, sulfuric acid, phosphoric acid, acetic acid, L-tartaric acid, citric acid, L-lactic acid, maleic acid, fumaric acid, succinic acid, methanesulfonic acid, benzenesulfonic acid, benzoic acid, p-toluenesulfonic acid, oxalic acid, p-nitrobenzoic acid, salicylic acid and 4-chlorobenzoic acid and the like.

TABLE 1

| Abbreviations | |
|---|---|
| Ac$_2$O: | acetic anhydride |
| AcOH: | acetic acid |
| CD3Cl-d3: | deuterated chloroform |
| DCM: | Dichloromethane |
| DMF: | Dimethylformamide |

TABLE 1-continued

| Abbreviations | |
|---|---|
| DMSO-d6: | deuterated dimethylsulfoxide |
| DPPA: | diphenylphosphoryl azide |
| EtOAC: | ethyl acetate |
| EtOH: | Ethanol |
| HPLC: | high performance liquid chromatography |
| hr or hrs: | hour or hours |
| Hz: | Hertz |
| kg: | Kilogram |
| L: | Liter |
| METHANOL-d4: | deuterated methanol |
| MHz: | Megahertz |
| mins: | Minutes |
| mmol: | Millimole |
| MS (ESI): | mass spectroscopy (electron spray ionization) |
| MTBE: | methyl tert-butyl ether |
| NaOH: | sodium hydroxide |
| NMM: | 4-methylmorpholine |
| NMR: | nuclear magnetic resonance |
| obsd.: | Observed |
| sat.: | Saturated |
| TEA: | Triethylamine |
| TEMPO: | 2,2,6,6-tetramethylpiperidinooxy |
| TFA: | trifluoroacetic acid |
| THF: | Tetrahydrofuran |

The problems in WO2013020993 A1 are solved according to present invention by a process for preparing the compounds of formula (I) shown in scheme 1:

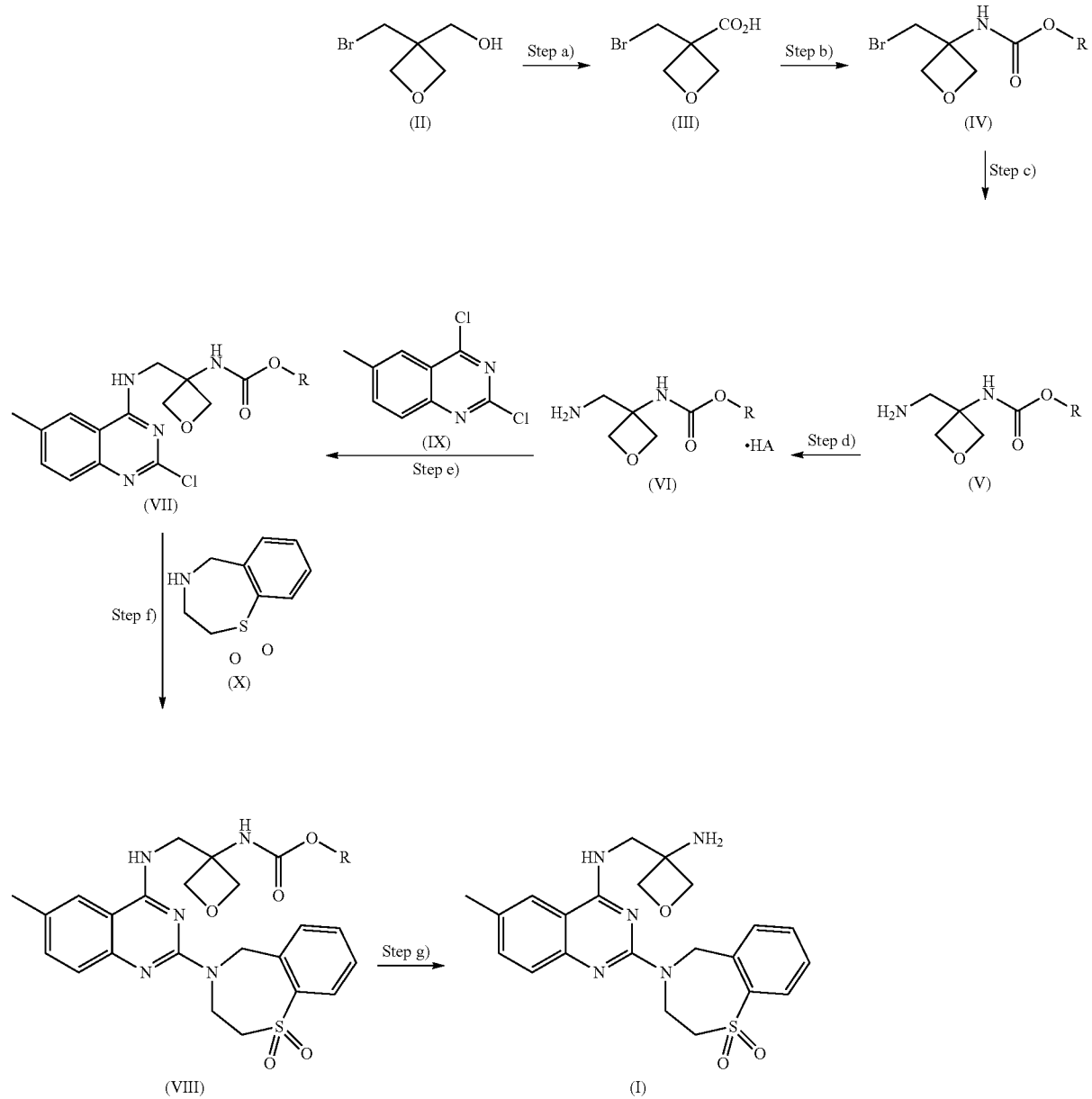

wherein R is $C_{1-6}$alkyl, $C_{1-6}$alkoxyphenyl-$C_xH_{2x}$— or phenyl-$C_xH_{2x}$—.

The invention relates to a process for the preparation of a compound of the formula (I):

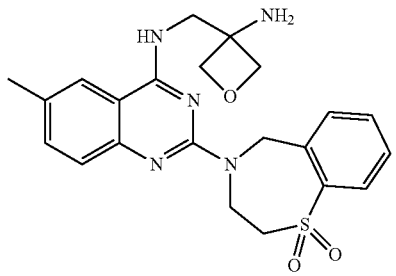
(I)

and pharmaceutically acceptable addition salts thereof, comprising the following steps:

step a) oxidation of [3-(bromomethyl)oxetan-3-yl]methanol of formula (II) to form a compound of formula (III),

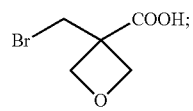
(III)

step b) conversion of carboxy group of a compound of formula (III) to carbamate to form a compound of formula (IV)

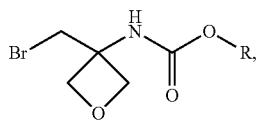
(IV)

wherein R is $C_{1-6}$alkyl, $C_{1-6}$alkoxyphenyl-$C_xH_{2x}$— or phenyl-$C_xH_{2x}$—;

step c) amination of a compound of formula (IV) to form a compound of formula (V)

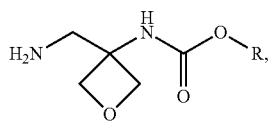
(V)

wherein R is as defined above;
step d) salt formation of a compound of formula (V) with an acid to form a compound of formula (VI)

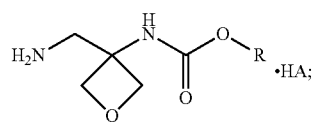
(VI)

wherein R is as defined above;

step e) substitution reaction of a compound of formula (VI) with a compound of formula (IX) to give a compound of formula (VII)

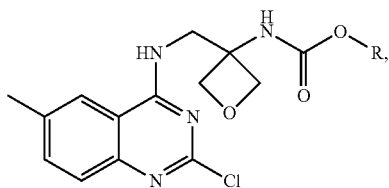
(VII)

wherein R is as defined above;
step f) substitution reaction of a compound of formula (VII) with a compound of formula (X) to give a compound of formula (VIII)

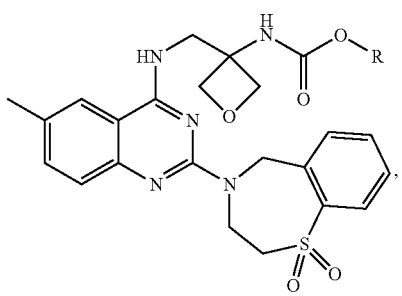
(VIII)

wherein R is as defined above;
step g) comprises deprotection of a compound of formula (VIII) to give a compound of formula (I)

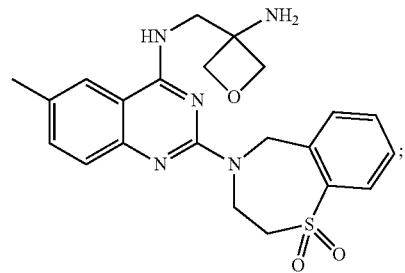
(I)

and if necessary, form a pharmaceutically acceptable addition salt.

The synthesis process steps (a), (b) and (c) result in compound of formula (V) which is a novel and is another important aspect of the present invention.

A detailed description of present invention of process steps is as following:

step a) comprises preparation of carboxylic acid of formula (III) by oxidizing [3-(bromomethyl)oxetan-3-yl]methanol of formula (II)

This reaction is performed with an oxidant at a reaction temperature range between 0° C. and 100° C., particularly between 15° C. to 25° C. The order of addition of reactants can be compelled by convenience.

The reaction can be conducted in various solvents, in particular, the reaction solvent is water, acetonitrile, dichloromethane, ethyl acetate or isopropyl acetate; or a co-solvent which is a mixture of two or more kinds of solvents selected from water, acetonitrile, dichloromethane, ethyl acetate and isopropyl acetate. More particular solvent is a co-solvent of water and acetonitrile.

The oxidant used in this reaction is sodium hypochlorite, potassium permanganate, 2,2,6,6-tetramethylpiperidinooxy or pyridinium chlorochromate; or a co-oxidant which is a mixture of two or more kinds of oxidants selected from sodium hypochlorite, potassium permanganate, 2,2,6,6-tetramethylpiperidinooxy and pyridinium chlorochromate. Particular oxidant is a co-oxidant of 2,2,6,6-tetramethylpiperidinooxy and sodium hypochlorite. The oxidation reaction is as a rule finished after 1 to 24 hours, particularly 4 to 6 hours.

step b) comprises the conversion of carboxylic acid of formula (III) to carbamate of formula (IV) through Curtius rearrangement.

The reaction is performed with an azide reagent and a base in an organic solvent and followed by adding an alcohol at temperature range of 0° C. and 100° C., particularly 80° C.

In this step, a compound of formula (III) is mixed with an azide reagent, particularly diphenylphosphoryl azide, and a base in an organic solvent to form an active intermediate 3-(bromomethyl)-3-isocyanato-oxetane, which can be further converted to carbamates of formula (IV) by adding various alcohols.

The base used in this reaction is triethylamine, diisopropylethylamine or 4-methyl morpholine, more particularly 4-methyl morpholine.

The reaction can be conducted in many organic solvents. In particular, the solvent used in step b) is acetonitrile, toluene, chlorobenzene, dichloromethane. More particular solvent is toluene.

The reaction temperature lies in the range of 0° C. and 100° C., particularly 80° C.

Typically, the alcohol used in step b) is tert-butanol, 2-methyl-2-butanol, benzyl alcohol or 4-methoxyphenylmethanol, particularly 4-methoxyphenylmethanol.

step c) comprises amination of compound of formula (IV) to form an amino compound of formula (V).

The reaction is performed with an amination agent, at reaction temperature range of 0° C. and 60° C., particularly in the rage of 25° C. and 30° C.

In order to form a primary amine, compound of formula (IV) and an amination reagent, particularly liquid ammonia, are charged to an autoclave to give the compound of formula (V).

Reaction temperature as a rule lies in the range of 0° C. and 60° C., particularly in the rage of 25° C. and 30° C.

The reaction is generally finished after 1 to 24 hours, particularly 8 hours.

step d) comprises salt formation of a compound of formula (V) with an acid to form a compound of formula (VI).

The acid used in this reaction includes various organic and inorganic acids, such as hydrochloric acid, hydrobromic acid, sulfuric acid, phosphoric acid, acetic acid, L-tartaric acid, citric acid, L-lactic acid, maleic acid, fumaric acid, succinic acid, methanesulfonic acid, benzenesulfonic acid, benzoic acid, p-toluenesulfonic acid, oxalic acid, p-nitrobenzoic acid, salicylic acid and 4-chlorobenzoic acid and the like, more particularly 4-chlorobenzoic acid.

step e) comprises the substitution reaction of a compound of formula (VI) with a compound of formula (IX) to give a compound of formula (VII).

The reaction can be performed in an organic solvent. In particular, the reaction is performed in tetrahydrofuran, 2-methyltetrahydrofuran or acetonitrile, more particularly in tetrahydrofuran.

The particular reaction temperature range is between 10° C. and 30° C.

step f) comprises the substitution reaction of a compound of formula (VII) with a compound of formula (X) to give a compound of formula (VIII). This reaction is performed in an organic solvent with an acid catalyst in temperature range between 0° C. and 100° C., particularly between 60° C. and 80° C.

The reaction is performed in an organic solvent. In particular, the reaction is performed in tetrahydrofuran, 2-methyltetrahydrofuran, acetonitrile, toluene, methanol, ethanol or iso-propanol, more particularly in ethanol.

Acid catalyst used in the reaction is hydrochloric acid, hydrobromic acid, sulfuric acid, phosphoric acid, methanesulfonic acid or ammonium chloride, particularly is ammonium chloride.

step g) comprises the deprotection of a compound of formula (VIII) to give a compound of formula (I). The reaction is performed in an organic solvent with acid in temperature range between 0° C. and 100° C., particularly between 10° C. and 40° C.

The organic solvent used in the reaction is dichloromethane, ethylacetate, isopropyl acetate, tetrahydrofuran or dioxane, particularly dichloromethane.

The acid used in the reaction is hydrochloric acid, hydrobromic acid, sulfuric acid, phosphoric acid, methanesulfonic acid or trifluoroacetic acid, particularly is or trifluoroacetic acid.

The invention is illustrated further by the following examples that are not be construed as limiting the invention in scope to the specific procedures described herein.

This invention further relates to a compound of formula (V):

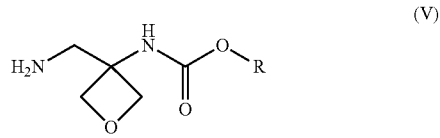

wherein R is $C_{1-6}$alkyl, $C_{1-6}$alkoxyphenyl-$C_xH_{2x}$— or phenyl-$C_xH_{2x}$—.

This invention is also relates to a compound of formula (III):

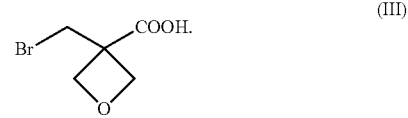

EXAMPLES

Example 1

Preparation of 3-(bromomethyl)oxetane-3-carboxylic acid

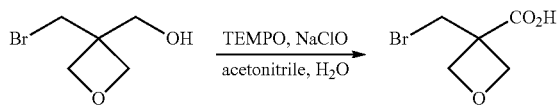

To a 100 ml flask was charged [3-(bromomethyl)oxetan-3-yl]methanol (17.3 g, 9.6 mmol) followed with 25 ml water and 5.3 mL of acetonitrile and TEMPO (153 mg, 0.96 mmol). The mixture was cooled to 10° C. 15.3 g sodium hypochloride (14%) was added over 10 min with the inner temperature maintained between 15° C. and 20° C. The reaction was stirred at room temperature till [3-(bromomethyl)oxetan-3-yl]methanol was consumed as monitored by HPLC. The resulted mixture was adjusted to pH 8-9 and extracted with 20 mL EtOAc twice. The aqueous layer was adjusted to pH 1-2 with 5N aqueous $H_2SO_4$ solution and extracted with dichloromethane. After removal of dichloromethane, 3-(bromomethyl)oxetane-3-carboxylic acid was obtained. MS obsd. (ESI$^+$) [(M+H)$^+$] 194. 1H NMR (400 MHz, METHANOL-d4) d ppm, 9.40-9.90 (s, 1H), 5.00-5.02 (d, J=6.8 Hz, 2H), 4.56-4.57 (d, J=6.8 Hz, 2H), 3.97 (s, 2H)

Example 2

Preparation of (4-methoxyphenyl)methyl N-[3-(bromomethyl)oxetan-3-yl]carbamate

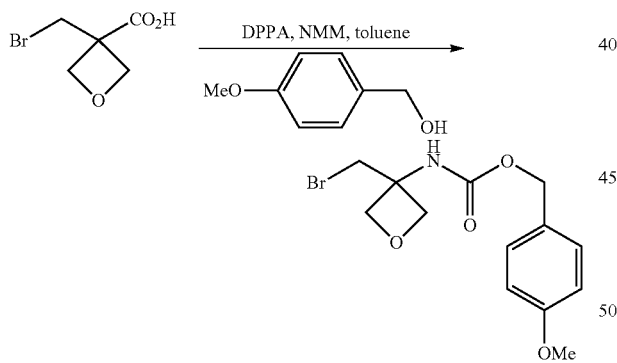

To a Reactor 1 was charged 3-(bromomethyl)oxetane-3-carboxylic acid (1.2 kg, 6.15 mol) followed by 6.4 kg toluene. The reaction mixture was cooled to 5° C. Then NMM (0.72 kg, 7.12 mol) was added to this reaction mixture slowly. After the addition, the solution was stirred 10 mins at room temperature.

To Reactor 2 was charged diphenylphosphoryl azide (1.76 kg, 6.39 mol) followed by 3.2 kg toluene. The mixture was heated to 80° C. Solution in Reactor 1 was added to Reactor 2 dropwise. After the addition, the reaction mixture was stirred for 30 mins at 80° C. To the reaction mixture was then added 4-methoxyphenylmethanol (0.82 kg, 5.94 mol) in 1.58 kg toluene solution slowly. After the addition, the reaction mixture was allowed to hold for 75 mins at 80° C. The reaction was monitored using HPLC. After reaction completion, the mixture was cooled to room temperature, and was washed with 6.0 kg water, 6.24 kg 4% sodium carbonate aqueous solution and 3.0 kg water sequentially. The organic phase was concentrated till dryness under reduced pressure and the residue was recrystallized in n-heptane/ethanol. The suspension was separated via centrifuge and the wet cake was washed with 1 kg n-heptane. The wet cake was dried under vacuum oven for 24 hours to afford title compound 1.46 kg, yield 72%. MS obsd. (ESI$^+$) [(M+H)$^+$] 330. 1H NMR (400 MHz, CD3Cl-d3) d ppm 7.30-7.33 (d, J=8.4 Hz, 2H), 6.91-6.93 (d, J=8.4 Hz, 2H), 5.33 (s, 1H), 5.06 (s, 2H), 4.70-4.72 (d, J=6.4 Hz, 2H), 4.51-4.53 (d, J=6.4 Hz, 2H), 4.00 (s, 2H), 3.84 (s, 3H).

Example 3

Preparation of tert-butyl N-[3-(bromomethyl)oxetan-3-yl]carbamate

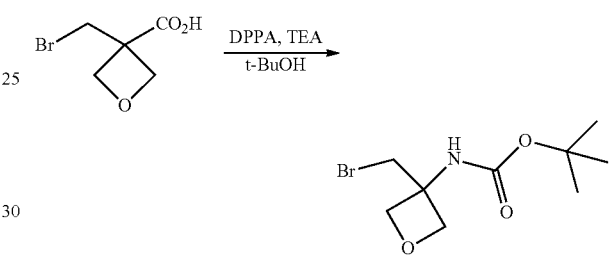

To a 50 ml flask was charged 3-(bromomethyl)oxetane-3-carboxylic acid (2.0 g, 10.3 mmol) followed by 20 mL of anhydrous t-butanol. The reaction mixture was cooled to 5° C. Then TEA (1.1 g, 11.3 mmol) was added. After the addition, DPPA (3.1 g, 10.8 mmol) was added in portions. The mixture was refluxed overnight. The organic phase was then concentrated till dryness under reduced pressure and the residue was dissolved in 30 ml EtOAc. The organic phase was washed with 10 mL $Na_2CO_3$ solution and 10 mL brine. After removal of solvents, tert-butyl N-[3-(bromomethyl)oxetan-3-yl]carbamate was obtained.

Example 4

Preparation of benzyl N-[3-(bromomethyl)oxetan-3-yl]carbamate

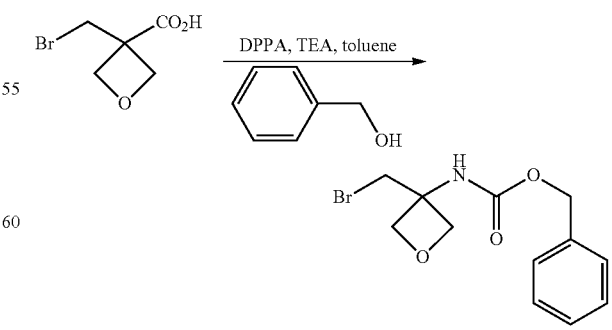

To a 100 ml flask was charged 3-(bromomethyl)oxetane-3-carboxylic acid (5.0 g, 25.6 mmol) followed by 50 mL of anhydrous toluene. Then TEA (2.87 g, 28.2 mmol) was added. After the addition of TEA, DPPA (7.64 g, 26.9 mmol) was added in portions. The mixture was heated at 65° C.-70° C. for 1 hour. To the reaction mixture was then added benzyl alcohol (4.2 g, 38.4 mmol) and heated at 80° C. for 2 hrs. The resulted mixture was cooled to room temperature and diluted with 50 ml EtOAc. The reaction mixture was washed with 30 mL water, 30 mL 10% Na$_2$CO$_3$ aqueous solution and 30 mL brine. The organic phase was concentrated to remove most of solvents under reduced pressure and 15 mL heptane was added. The suspension was stirred at room temperature for 2 hours and was separated by filtration. The wet cake was dried under vacuum oven to afford 4.95 g benzyl N-[3-(bromomethyl)oxetan-3-yl]carbamate.

Example 5

Preparation of 1,1-dimethylpropyl N-[3-(bromomethyl)oxetan-3-yl]carbamate

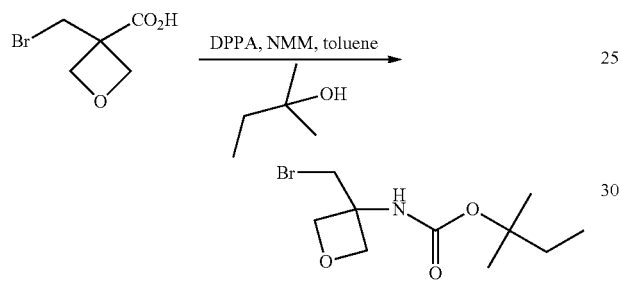

To a 250 ml flask was charged 3-(bromomethyl)oxetane-3-carboxylic acid (20.4 g, 100 mmol) followed by 120 mL of anhydrous toluene. NMM (12.1 g, 120 mmol) was added over 10 min. After the addition, DPPA (30.3 g, 110 mmol) in 80 ml toluene was added over 30 min. The mixture was heated at 80° C.-85° C. for 40 min. To the reaction mixture was then added t-amyl alcohol (44 g, 150 mmol) and heated at 80° C. for 3 hrs. The resulted mixture was cooled to room temperature and was washed with 100 mL water, 30 mL 10% Na$_2$CO$_3$ aqueous solution and 30 mL brine. The organic phase was concentrated in vacuum and the crude product was purified by flash chromatography. The product was slurried in heptane. After filtration and drying, 12.3 g 1,1-dimethylpropyl N-[3-(bromomethyl)oxetan-3-yl]carbamate was obtained.

Example 6

Preparation of (4-methoxyphenyl)methyl N-[3-(bromomethyl)oxetan-3-yl]carbamate

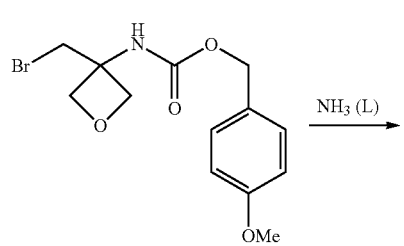

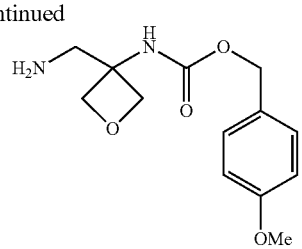

To a 10 L autoclave was charged (4-methoxyphenyl)methyl N-[3-(bromomethyl)oxetan-3-yl]carbamate (1.1 kg, 3.33 mol) and 5.5 L liquid ammonia. The reaction mixture was stirred at 25° C.-30° C. for 8 hours. Then the ammonia was released carefully. To the residue was added 5.5 L 2-methyltetrahydrofuran. The mixture was transferred into a separation funnel. To the mixture was then added 1.1 L 3N NaOH solution. The aqueous phase was extracted with 4.4 L 2-methyltetrahydrofuran. The combined organic phase was washed with 1.1 L saturated NaCl aqueous solution twice. After phase separation, organic phase was concentrated under vacuum to about 1 L. The crude residual was used directly without further purification.

Example 7

Preparation of (4-methoxyphenyl)methyl N-[3-(bromomethyl)oxetan-3-yl]carbamate

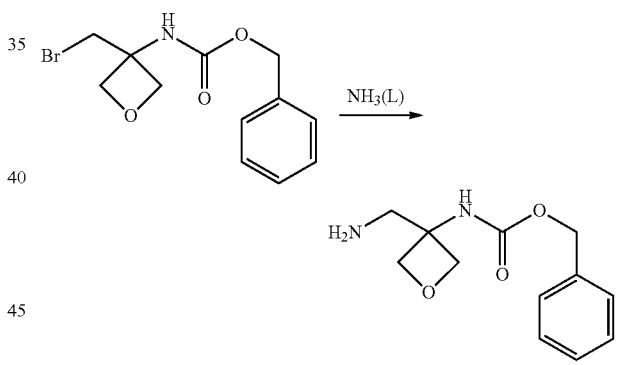

The titled compound is prepared in analogy to Example 6 by using benzyl N-[3-(bromomethyl) oxetan-3-yl]carbamate, which is prepared in Example 4, instead of (4-methoxyphenyl)methyl N-[3-(bromomethyl)oxetan-3-yl]carbamate, Example 8

Preparation of 1,1-dimethylpropyl N-[3-(aminomethyl)oxetan-3-yl]carbamate

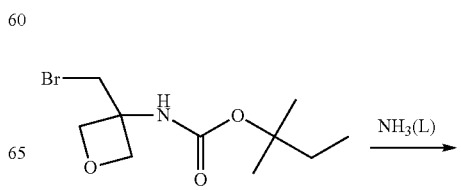

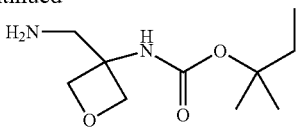

The titled compound is prepared in analogy to Example 6 by using 1,1-dimethylpropyl N-[3-(bromomethyl)oxetan-3-yl]carbamate, which is prepared in Example 5, instead of (4-methoxyphenyl)methyl N-[3-(bromomethyl)oxetan-3-yl]carbamate.

Example 9

Preparation of tert-butyl N-[3-(aminomethyl)oxetan-3-yl]carbamate

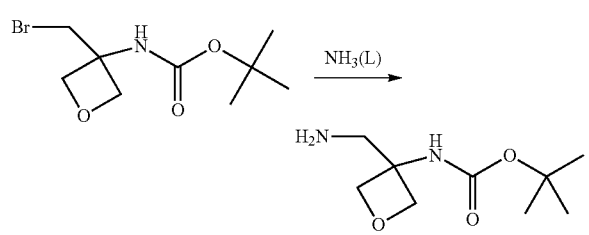

The titled compound is prepared in analogy to Example 6 by using tert-butyl N-[3-(bromomethyl)oxetan-3-yl]carbamate, which is prepared in Example 3, instead of (4-methoxyphenyl)methyl N-[3-(bromomethyl)oxetan-3-yl]carbamate.

Example 10

Preparation of (4-methoxyphenyl)methyl N-[3-(bromomethyl)oxetan-3-yl]carbamate 4-chlorobenzoic acid salt

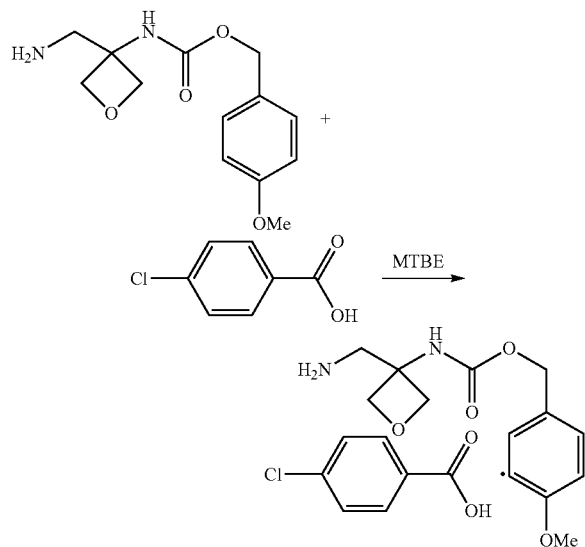

To the residue from Example 6 was then added 4-chlorobenzoic acid (420 g, 2.68 mol) and 2 L MTBE. The mixture was stirred at 15° C.-25° C. for 14 hours. Vacuum filtration to collect the solid and the wet cake was washed with 1 L MTBE. The wet cake was dried under vacuum oven for 24 hours to afford 0.81 kg desired salt with yield 57.5%. MS obsd. (ESI+) [(M+H)+] 423. 1H NMR (400 MHz, DMSO-d6) δ ppm 8.32 (s, 1H), 7.88-7.91 (d, J=8.4 Hz, 2H), 7.42-7.45 (d, J=8.4 Hz, 2H), 7.29-7.31 (d, J=8.4 Hz, 2H), 6.90-6.92 (d, J=8.4 Hz, 2H), 4.94 (s, 2H), 4.54-4.56 (d, J=6.4 Hz, 2H), 4.44-4.45 (d, J=6.4 Hz, 2H), 3.75 (s, 3H), 3.19 (s, 2H).

Example 11

Preparation of (4-methoxyphenyl)methyl N-[3-[[(2-chloro-6-methyl-quinazolin-4-yl)amino]methyl]oxetan-3-yl]carbamate

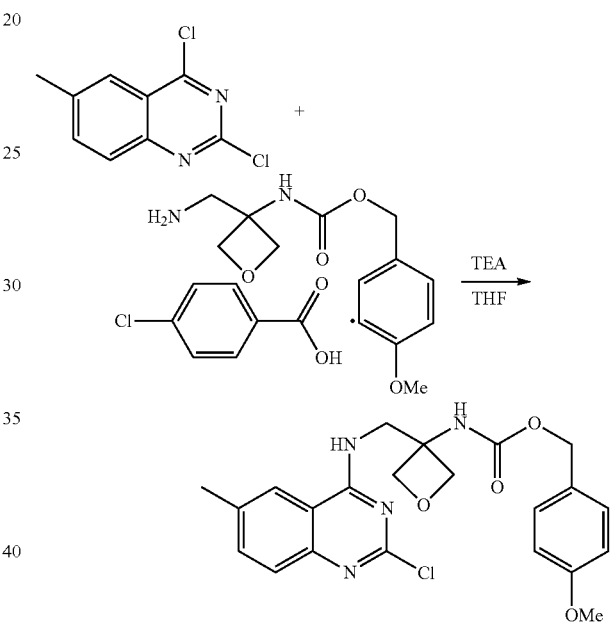

To a 250 L glass-lined reactor was charged (4-methoxyphenyl)methyl N-[3-(bromomethyl)oxetan-3-yl]carbamate 4-chlorobenzoic acid salt (8.1 kg, 19.2 mol) and 61.6 kg tetrahydrofuran. To the solution was then added TEA (5.9 kg, 58.3 mol). The mixture was then cooled to 10° C.-15° C. To the mixture was then added 2,4-dichloro-6-methyl-quinazoline (3.99 kg, 18.7 mol) while control reaction temperature at 10° C.-30° C. The reaction mixture was then stirred at 22° C.-27° C. for 20 hours. HPLC was used to monitor the reaction. After reaction completion, the reaction mixture was concentrated in vacuum below 40° C. to 24.3-32.4 L over 3.5 hours while maintaining the bath temperature at 15° C.-25° C. To the residue was then added 80.2 kg water over 100 mins. The mixture was stirred at 15° C.-25° C. for 3.5 hours. The suspension was separated using centrifuge and washed with 48 kg water in four portions over 50 mins to afford 23.6 kg wet (4-methoxyphenyl)methyl N-[3-[[(2-chloro-6-methyl-quinazolin-4-yl)amino]methyl]oxetan-3-yl]carbamate.

To a 250 L glass-lined reactor was charged 23.6 kg wet (4-methoxyphenyl)methyl N-[3-[[(2-chloro-6-methyl-quinazolin-4-yl)amino]methyl]oxetan-3-yl]carbamate, 24.0 kg MTBE and 7.0 kg ethylacetate. The mixture was stirred at 15° C.-25° C. for 2.5 hours. The suspension was separated via centrifuge and washed with 6.0 kg MTBE. The wet cake was dried under vacuum oven at 38° C.-42° C. with a nitrogen bleed for 3 hours and then 40° C.-52° C. for 17 hours to afford 7.9 kg title compound with yield 92%. MS obsd. (ESI$^+$) [(M+H)$^+$] 443. 1H-NMR (400 Hz, DMSO-d6) d ppm 8.67-8.69 (t, J=5.6 Hz, 1H), 8.09 (s, 1H), 7.85 (s, 1H), 7.64-7.67 (m, 1H), 7.53-7.55 (m, 1H), 7.26-7.29 (d, J=8.4 Hz, 2H), 6.88-6.90 (d, J=8.4 Hz, 2H), 4.96 (s, 2H), 4.62-4.64 (d, J=6.4 Hz, 2H), 4.51-4.53 (d, J=6.4 Hz, 2H), 4.07-4.09 (d, J=6.4 Hz, 2H), 3.74 (s, 3H), 2.47 (s, 3H).

Example 12

Preparation of (4-methoxyphenyl)methyl N-[3-[[[2-(1,1-dioxo-3,5-dihydro-1,4-benzothiazepin-4-yl)-6-methyl-quinazolin-4-yl]amino]methyl]oxetan-3-yl] carbamate Preparation of intermediate formula (X): 2,3,4,5-Tetrahydro-1,4-benzothiazepine-1,1-dioxide:

(X)

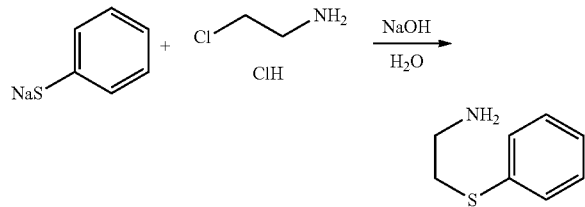

Step 1: Preparation of 2-phenylsulfanylethanamine

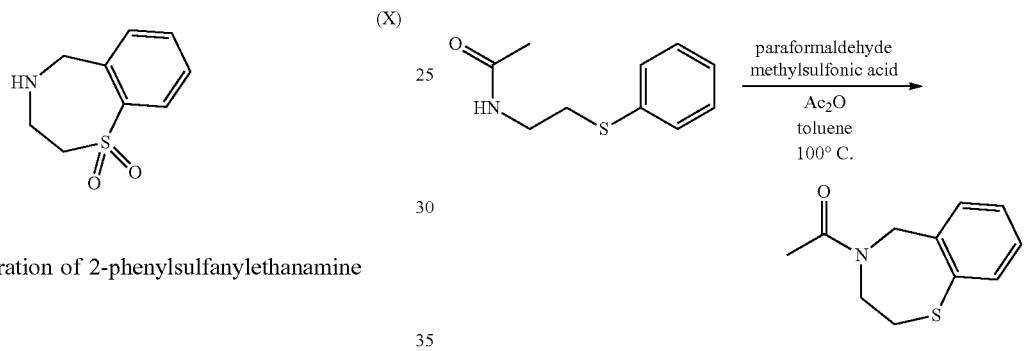

To a reactor was charged 56.1 kg of water followed by NaOH (7.0 kg, 175 mol). Start the mechanical stirrer until all NaOH dissolved to form a solution. Cool the solution to 25° C. and to the solution was added sodium thiophenoxide (50.7 kg, aqueous solution) and 2-chloroethylamine hydrochloride (17.7 kg, 153 mol). The mixture was stirred at 25° C. for 15 hours. HPLC was used to monitor the reaction. After reaction completion, the reaction mixture was extracted with 61.1 kg EtOAc twice. The combined organic phase was concentrated to about 92 L and used in next step without further purification.

Step 2: Preparation of N-(2-phenyl sulfanylethyl)acetamide

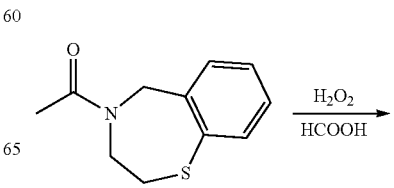

The residue of last step was heated to 45° C. and to the solution was slowly added AcOH (14.0 kg, 233 mol) while control the reaction temperature below 60° C. The reaction was monitored by HPLC. After reaction completion, the solution was cooled to 45° C. and concentrated under vacuum to remove 55 L EtOAc. The mixture was then cooled to below 25° C. and to the solution was slowly added 62.0 kg n-heptane. After addition, the suspension was cooled to 0° C. and held for 1 hour. The solid was collected by centrifuge.

The wet cake was dried under vacuum oven for 22 hours to afford 22.2 kg of N-(2-phenylsulfanylethyl) acetamide with 74% yield. MS obsd. (ESI$^+$) [(M+H)$^+$] 196. 1H-NMR (400 Hz, DMSO-d6) d ppm 8.07 (s, 1H), 7.18-7.40 (m, 5H), 3.21-3.26 (m, 2H), 2.99-3.03 (m, 2H), 1.80 (s, 3H).

Step 3: Preparation of 1-(3,5-dihydro-2H-1,4-benzothiazepin-4-yl)ethanone

To a reactor was charged N-(2-phenylsulfanylethyl) acetamide (22.2 kg, 114 mol) and 124.7 kg toluene. To the solution was then added paraformaldehyde (2.1 kg, 70 mol), methylsulfonic acid (10.9 kg, 113 mol) and Ac$_2$O (14.0 kg, 137 mol). The reaction mixture was heated to 75° C.-80 and to the reactor was then charged paraformaldehyde (4.9 kg, 163 mol) portionwise while control reaction temperature lower than 80° C. After the addition, the reaction mixture was heated to 100° C.-105° C. and held for 1 hour. The reaction was monitored by HPLC. After reaction completion, the reaction mixture was cooled to 30° C. and to the reactor was added 71.1 kg water. Phase separation and the organic solution was washed with 63.1 kg saturated NaHCO$_3$ aqueous solution followed by 63.1 kg brine solution. The organic phase was then concentrated under vacuum to remove all the organic solvent and the residue was used directly for next step without further purification.

Step 4: Preparation of 1-(1,1-dioxido-2,3-dihydro-1,4-benzothiazepin-4(5H)-yl)ethanone

17

-continued

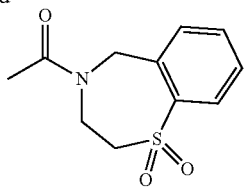

5

To the left residue of last step was added 112.8 kg formic acid and 12.8 kg water. The mixture was cooled to 0° C. To the reaction mixture was slowly added 80.4 kg H$_2$O$_2$ (35%) while control reaction temperature lower than 10° C. After addition, the reaction mixture was stirred for 1 hour at 10° C. Then the reaction mixture was raised to 25° C. and stirred for 3 hours. The reaction was monitored using HPLC. After reaction completion, to the reaction mixture was added 177.3 kg water and 235.1 kg DCM. Phase separation and the aqueous layer was extracted with 165.9 kg DCM again. The combined organic phase was washed with 112.7 kg sat. Na$_2$SO$_3$ aqueous solution, 112.1 kg sat. Na$_2$CO$_3$ aqueous solution and 103.0 kg sat. NaCl aqueous solution. The organic phase was then concentrated under vacuum to remove all the organic solvent. The residue was then dispersed in 54.3 kg EtOH and stirred for 1 hour at 55° C.-65° C. The suspension was separated by centrifuge and the wet cake was dried under vacuum oven for 12 hours to afford 17.4 kg 1-(1,1-dioxido-2,3-dihydro-1,4-benzothiazepin-4(5H)-yl)ethanone with yield 64%. MS obsd. (ESI$^+$) [(M+H)$^+$] 240. 1H-NMR (400 Hz, DMSO-d6) d ppm 7.92-8.00 (m, 1H), 7.55-7.74 (m, 3H), 4.60-4.88 (m, 2H), 4.05 (brs, 2H), 3.48-3.70 (m, 2H), 3.53 (d, J=8.0 Hz, 3H).

Step 5: Preparation of 2,3,4,5-tetrahydro-1,4-benzothiazepine-1,1-dioxide

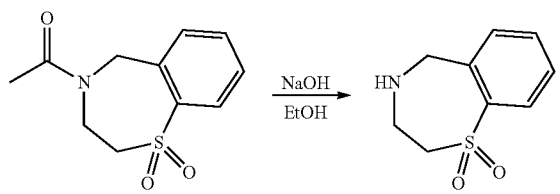

To a reactor was charged 1-(1,1-dioxido-2,3-dihydro-1,4-benzothiazepin-4(5H)-yl)ethanone (16.6 kg, 69.4 mol), 55.2 kg EtOH and 55. 8 kg NaOH aqueous solution (11.1 kg NaOH in 44.7 kg H$_2$O). The reaction mixture was heated to 74-79° C. and held for 24 hours at this temperature. The reaction was monitored using HPLC. After reaction completion, the mixture was cooled to 50° C.-55° C. and the organic solvent was removed under reduced pressure. To the reactor was then added 104.1 kg water and the mixture was cooled to 0° C.-7° C. and held for 1 hour. The suspension was separated using centrifuge and the wet cake was washed with 44.7 kg water twice. The wet cake was dried under vacuum oven for 24 hours to afford 9.9 kg 2,3,4,5-tetrahydro-1,4-benzothiazepine 1,1-dioxide with 72.3% yield. MS obsd. (ESI$^+$) [(M+H)$^+$] 198. 1H-NMR (400 Hz, DMSO-d6) d ppm 7.89 (dd, J=1.2, 7.6 Hz, 1H), 7.56 (t, J=7.6 Hz, 1H), 7.47 (t, J=7.6 Hz, 1H), 7.42 (d, J=7.6 Hz, 1H), 4.04 (s, 2H), 3.30-3.32 (m, 2H), 3.25-3.30 (m, 2H), 2.64 (s, 1H).

18

Preparation of (4-methoxyphenyl) methyl N-[3-[[[2-(1,1-dioxo-3,5-dihydro-1,4-benzothiazepin-4-yl)-6-methyl-quinazolin-4-yl]amino]methyl]oxetan-3-yl] carbamate

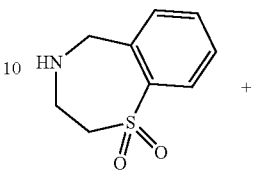

+

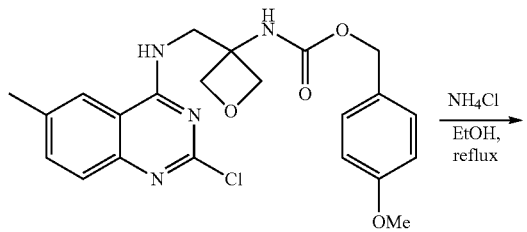

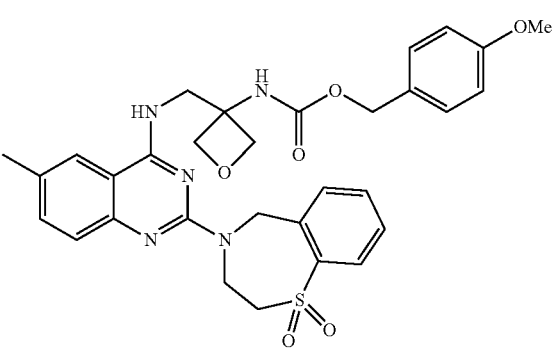

To a 250 L glass-lined reactor was charged 63 kg EtOH followed by (4-methoxyphenyl)methyl N-[3-[[(2-chloro-6-methyl-quinazolin-4-yl)amino]methyl]oxetan-3-yl]carbamate (7.8 kg, 17.6 mol), 2,3,4,5-tetrahydro-1,4-benzothiazepine-1,1-dioxide (3.89 kg, 19.7 mol) and ammonium chloride (49 g, 0.92 mol). The reaction mixture was stirred at 68° C.-72° C. for 20 hours. HPLC was used to monitor the reaction. After reaction completion, the reaction mixture was slowly cooled to 20° C.-25° C. The solids were collected by vacuum filtration and washed with 15.6 kg EtOH in two portions. The wet cake was dried in a vacuum oven with a nitrogen bleed at 38° C.-42° C. for about 4 hours and then heated to 50° C.-55° C. for 30 hours to afford 11.0 kg title compound with yield 88%. MS obsd. (ESI$^+$) [(M+H)$^+$] 604. 1H-NMR (400 Hz, DMSO) d ppm 9.57 (s, 1H), 8.14 (s, 1H), 7.93-7.95 (d, 1H, J=8), 7.68 (m, 3H), 7.57-7.58 (m, 1H), 7.22-7.23 (d, 2H, J=4), 7.68-7.69 (d, 2H, J=4), 4.98-5.17 (m, 2H), 4.26-4.68 (m, 5H), 3.74-4.1 (m, 3H), 3.4-3.46 (t, 1H, J=8), 2.51 (s, 3H), 2.39 (s, 3H).

Example 13

Preparation of N-[(3-aminooxetan-3-yl) methyl]-2-(1,1-dioxo-3,5-dihydro-1,4-benzothiazepin-4-yl)-6-methyl-quinazolin-4-amine

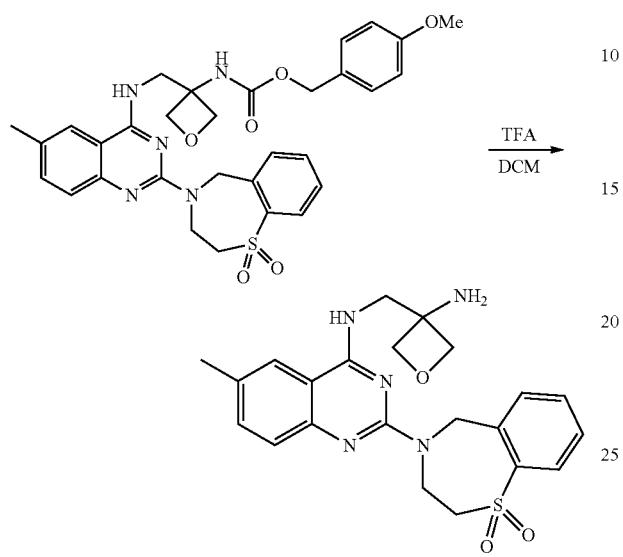

To a 250 L glass-lined reactor was charged N-[3-[[[2-(1,1-dioxo-3,5-dihydro-1,4-benzothiazepin-4-yl)-6-methyl-quinazolin-4-yl]amino]methyl]oxetan-3-yl]carbamate (10.8 kg, 24.6 mol) and 120 kg dichloromethane. To the mixture was then added 16.0 kg 1N NaOH solution in portions. After phase separation, the aqueous phase was extracted with 14.0 kg dichloromethane. The combined organic phase was washed with 25 kg 20% NaCl aqueous solution, then was transferred to a 100 L glass-lined reactor and concentrated to 30-35 L below 35° C. in vacuum to prepare Solution 1.

To another 250 L glass-lined reactor were charged with 26.0 kg dichloromethane and 16.0 kg trifluoroacetic acid. The mixture was cooled to 15° C.-20° C. and to the solution was added the titled Solution 1 in portions. The mixture was stirred for 30 mins at 15° C.-25° C. and then cooled to 0° C.-10° C. To the mixture was added 39.8 kg DMF and then the solution was concentrated to 62-65 L between 15° C.-30° C. in vacuum for over 16.5 hours to afford Solution 2.

To a 300 L glass-lined reactor was charged 128.3 kg 1.5N NaOH solution and cooled to 5° C.-7° C. To the reactor was then added 3.0 kg dimethylformamide followed by Solution 2. The suspension was stirred at 7° C.-11° C. for 30 mins. The solid was collected by vacuum filtration and washed with 101 kg water. Then the wet solid was charged into a 250 L glass-lined reactor followed by 54.0 kg EtOH. The mixture was heated to 74° C.-78° C. and stirred for 4.5 hours. The mixture was then cooled to 20° C.-25° C. The solid was collected by vacuum filtration and the wet cake was washed with 15.0 kg EtOH. The wet cake was dried in vacuum oven at 48° C.-52° C. with nitrogen bleed for 20 hours to afford 5.82 kg title compound with yield 85%. MS obsd. (ESI$^+$) [(M+H)$^+$] 440. 1H-NMR (400 Hz, METHANOL-D4) d ppm 7.98 (d, J=7.6 Hz, 1H), 7.86 (d, J=7.6 Hz, 1H), 7.73 (s, 1H), 7.60 (t, J=7.6 Hz, 1H), 7.32-7.47 (m, 3H), 5.53 (s, 2H), 4.58 (brs, 2H), 3.84 (s, 2H), 3.53 (t, J=4.8 Hz, 2H), 2.41 (2, 3H), 2.21 (m, 2H), 1.97-2.04 (m, 2H), 1.82-1.91 (m, 2H).

The invention claimed is:

1. A process for the preparation of a compound of the formula (V):

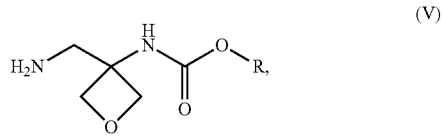

wherein R is $C_{1-6}$alkyl, $C_{1-6}$alkoxyphenyl-$C_xH_{2x}$— or phenyl-$C_xH_{2x}$—, and wherein x is 1 to 6, the process comprising the following steps:

Step a) converting a carboxy group to a carbamate to form a compound of formula (III)

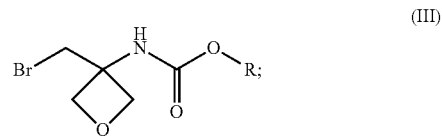

Step b) aminating a compound of formula (III) to form a compound of formula (V)

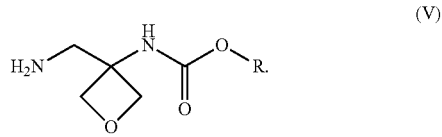

2. A compound of formula (V):

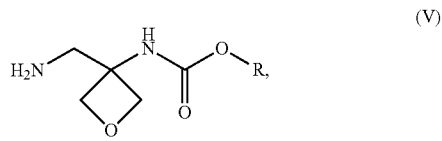

wherein R is $C_{1-6}$alkyl, $C_{1-6}$alkoxyphenyl-$C_xH_{2x}$— or phenyl-$C_xH_{2x}$—, and wherein x is 1 to 6.

3. A compound having the structure:

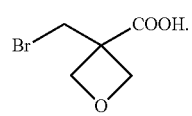

* * * * *